(12) United States Patent
Caldarone et al.

(10) Patent No.: US 7,717,855 B2
(45) Date of Patent: May 18, 2010

(54) SYSTEM FOR PERFORMING REMOTE ISCHEMIC PRECONDITIONING

(75) Inventors: Christopher Caldarone, Toronto (CA); Andrew Redington, Toronto (CA)

(73) Assignee: The Hospital for Sick Children, Toronto (CA)

( * ) Notice: Subject to any disclaimer, the term of this patent is extended or adjusted under 35 U.S.C. 154(b) by 0 days.

(21) Appl. No.: 11/634,749

(22) Filed: Dec. 6, 2006

(65) Prior Publication Data
US 2008/0139949 A1    Jun. 12, 2008

(51) Int. Cl.
*A61B 5/02* (2006.01)
*A61B 17/00* (2006.01)

(52) U.S. Cl. .............. 600/496; 600/490; 600/495; 606/201; 606/202

(58) Field of Classification Search .......... 600/481, 600/483, 485, 490–504; 606/201–203
See application file for complete search history.

(56) References Cited

U.S. PATENT DOCUMENTS

| | | | |
|---|---|---|---|
| 3,552,383 A | | 1/1971 | Krueger et al. |
| 4,106,002 A | | 8/1978 | Hogue, Jr. |
| 4,206,764 A | | 6/1980 | Williams |
| 4,321,929 A | | 3/1982 | Lemelson et al. |
| 4,664,651 A | * | 5/1987 | Weinshenker et al. ........ 604/115 |
| 5,135,003 A | | 8/1992 | Souma |
| 5,267,565 A | * | 12/1993 | Beard ........................ 600/454 |
| 5,571,075 A | | 11/1996 | Bullard et al. |
| 5,634,467 A | | 6/1997 | Nevo |
| 5,651,369 A | | 7/1997 | Tomita |
| 6,152,881 A | * | 11/2000 | Raines et al. ............... 600/507 |
| 6,210,423 B1 | * | 4/2001 | Kim ........................ 606/203 |
| 6,485,429 B2 | | 11/2002 | Forstner |
| 6,550,482 B1 | | 4/2003 | Burbank et al. |
| 6,626,840 B2 | | 9/2003 | Drzewiecki et al. |
| 6,719,704 B2 | | 4/2004 | Narimatsu et al. |
| 6,858,012 B2 | * | 2/2005 | Burns et al. ............... 600/483 |
| 6,962,599 B2 | * | 11/2005 | Hui ........................... 606/202 |
| 7,004,907 B2 | | 2/2006 | Banet et al. |
| 7,018,335 B2 | | 3/2006 | Kario et al. |
| 7,048,702 B2 | | 5/2006 | Hui |

(Continued)

FOREIGN PATENT DOCUMENTS

EP        0 960 598 A1    12/1999

(Continued)

OTHER PUBLICATIONS

Bartekova et al., Liver ischemia induced remote preconditioning: role of cardioprotective proteins. 25. ISHR-ES meeting. Jun. 21-25, 2005. Tromsoe, Norway. J Mol Cell Cardiol. 2005;38(6):1004.

(Continued)

*Primary Examiner*—Charles A Marmor, II
*Assistant Examiner*—Navin Natnithithadha
(74) *Attorney, Agent, or Firm*—Wolf, Greenfield & Sacks, P.C.

(57) ABSTRACT

A system for remote ischemic preconditioning that includes a cuff, and actuator, and a controller that operates the actuator according to a treatment protocol. The treatment protocol includes a plurality of treatment cycles that each comprise cuff actuation, an ischemic duration, cuff release, and a reperfusion duration.

33 Claims, 3 Drawing Sheets

U.S. PATENT DOCUMENTS

| | | | |
|---|---|---|---|
| 7,314,478 B2* | 1/2008 | Hui | 606/202 |
| 7,338,410 B2 | 3/2008 | Dardik | |
| 7,374,540 B2* | 5/2008 | Schnall | 600/481 |
| 7,390,303 B2* | 6/2008 | Dafni | 600/500 |
| 2001/0029389 A1* | 10/2001 | Kim | 606/203 |
| 2003/0013974 A1 | 1/2003 | Nagarajan et al. | |
| 2003/0065270 A1* | 4/2003 | Raines et al. | 600/504 |
| 2003/0176795 A1 | 9/2003 | Harris et al. | |
| 2003/0233118 A1 | 12/2003 | Hui | |
| 2004/0044290 A1 | 3/2004 | Ward et al. | |
| 2004/0064076 A1 | 4/2004 | Bilgi et al. | |
| 2004/0102818 A1 | 5/2004 | Hakky et al. | |
| 2004/0241634 A1 | 12/2004 | Millis et al. | |
| 2004/0255956 A1 | 12/2004 | Vinten-Johansen et al. | |
| 2005/0004476 A1 | 1/2005 | Payvar et al. | |
| 2005/0159640 A1 | 7/2005 | Barbut et al. | |
| 2005/0177078 A1 | 8/2005 | Loeb et al. | |
| 2006/0052712 A1 | 3/2006 | Poliac et al. | |
| 2006/0052713 A1 | 3/2006 | Poliac et al. | |
| 2006/0052714 A1 | 3/2006 | Poliac et al. | |
| 2006/0058717 A1 | 3/2006 | Hui et al. | |
| 2006/0100639 A1 | 5/2006 | Levin et al. | |
| 2006/0142663 A1 | 6/2006 | Sawanoi et al. | |
| 2009/0137884 A1 | 5/2009 | Naghavi et al. | |

FOREIGN PATENT DOCUMENTS

| | | |
|---|---|---|
| RU | 2 253 429 C1 | 6/2005 |
| WO | WO 83/00995 A1 | 3/1983 |
| WO | WO 2005/011503 A1 | 2/2005 |
| WO | WO 2005/077265 A1 | 8/2005 |
| WO | WO 2006/024871 A1 | 3/2006 |
| WO | WO 2006/030441 A2 | 3/2006 |
| WO | WO 2006/061825 A2 | 6/2006 |
| WO | WO 2008/148045 A1 | 12/2008 |
| WO | WO 2008/148062 A1 | 12/2008 |

OTHER PUBLICATIONS

Brzozowski et al., Ischemic preconditioning of remote organs attenuates gastric ischemia-reperfusion injury through involvement of prostaglandins and sensory nerves. Eur J Pharmacol. Sep 19, 2004;499(1-2):201-13.

Cheung et al., Randomized controlled trial of the effects of remote ischemic preconditioning on children undergoing cardiac surgery: first clinical application in humans. J Am Coll Cardiol. Jun 6, 2006;47(11):2277-82.

Dickson et al., Rabbit heart can be "preconditioned" via transfer of coronary effluent. Am J Physiol. Dec. 1999;277(6 Pt 2):H2451-7.

Dong et al., Limb ischemic preconditioning reduces infarct size following myocardial ischemia-reperfusion in rats Sheng Li Xue Bao. Feb. 25, 2004;56(1):41-6. Chinese.

Gho et al., Myocardial protection by brief ischemia in noncardiac tissue. Circulation. Nov. 1, 1996;94(9):2193-200.

Jenkins et al., Ischaemic preconditioning reduces troponin T release in patients undergoing coronary artery bypass surgery. Heart. Apr. 1997;77(4):314-8.

Kharbanda et al., Transient limb ischemia induces remote ischemic preconditioning in vivo. Circulation. Dec. 3, 2002;106(23):2881-3.

Kharbanda et al., Ischemic preconditioning prevents endothelial injury and systemic neutrophil activation during ischemia-reperfusion in humans in vivo. Circulation. Mar. 27, 2001;103(12):1624-30.

Konstantinov et al., Remote ischemic preconditioning of the recipient reduces myocardial ischemia-reperfusion injury of the denervated donor heart via a Katp channel-dependent mechanism. Transplantation. Jun. 27, 2005;79(12):1691-5.

Konstantinov et al., The remote ischemic preconditioning stimulus modifies inflammatory gene expression in humans. Physiol Genomics. Sep. 16, 2004;19(1):143-50. Epub Aug. 10, 2004.

Konstantinov et al., The remote ischemic preconditioning stimulus modifies gene expression in mouse myocardium. J Thorac Cardiovasc Surg. Nov. 2005;130(5):1326-32.

Lang et al., Myocardial preconditioning and remote renal preconditioning—identifying a protective factor using proteomic methods? Basic Res Cardiol. Mar. 2006;101(2):149-58. Epub Nov. 11, 2005.

Laskey et al., Frequency and clinical significance of ischemic preconditioning during percutaneous coronary intervention. J Am Coll Cardiol. Sep. 17, 2003;42(6):998-1003.

Leesar et al., Preconditioning of human myocardium with adenosine during coronary angioplasty. Circulation. Jun. 3, 1997;95(11):2500-7.

Leesar et al., Nonelectrocardiographic evidence that both ischemic preconditioning and adenosine preconditioning exist in humans. J Am Coll Cardiol. Aug. 6, 2003;42(3):437-45.

Loukogeorgakis et al., Remote ischemic preconditioning provides early and late protection against endothelial ischemia-reperfusion injury in humans: role of the autonomic nervous system. J Am Coll Cardiol. Aug. 2, 2005;46(3):450-6.

McCully et al., Adenosine-enhanced ischemic preconditioning: adenosine receptor involvement during ischemia and reperfusion. Am J Physiol Heart Circ Physiol. Feb. 2001;280(2):H591-602.

Peng et al., The protective effects of ischemic and calcitonin gene-related peptide-induced preconditioning on myocardial injury by endothelin-1 in the isolated perfused rat heart. Life Sci. 1996;59(18):1507-14.

Penttila et al., Ischemic preconditioning does not improve myocardial preservation during off-pump multivessel coronary operation. Ann Thorac Surg. Apr. 2003;75(4):1246-52; discussion 1252-3.

Peralta et al., Liver ischemic preconditioning: a new strategy for the prevention of ischemia-reperfusion injury. Transplant Proc. Aug. 2003;35(5):1800-2.

Przyklenk et al., Regional ischemic 'preconditioning' protects remote virgin myocardium from subsequent sustained coronary occlusion. Circulation. Mar. 1993;87(3):893-9.

Schoemaker et al., Bradykinin mediates cardiac preconditioning at a distance. Am J Physiol Heart Circ Physiol. May 2000;278(5):H1571-6.

Tomai et al., Ischemic preconditioning in humans: models, mediators, and clinical relevance. Circulation. Aug. 3, 1999;100(5):559-63.

Wolfrum et al., Calcitonin gene related peptide mediates cardioprotection by remote preconditioning. Regul Pept. Apr. 15, 2005;127(1-3):217-24.

English Language Translation of RU 2253429.

Nandagopal, K. et al., "Critical Role for Nitric Oxide Signaling in Cardiac and Neuronal Ischemic Preconditioning and Tolerance", *JPET* 297:474-478, 2001.

* cited by examiner

SYSTEM FOR PERFORMING REMOTE ISCHEMIC PRECONDITIONING

FIELD

The invention relates to systems for performing remote ischemic preconditioning.

DISCUSSION OF RELATED ART

Ischemic diseases are significant causes of mortality in industrialized nations. It is well established that tissue damage results from ischemia (stoppage of blood flow to the tissue) followed by reperfusion (reflow of blood to the tissue). Ischemia and reperfusion causes disturbance of microcirculation with ensuing tissue damage and organ dysfunction. Organs such as the kidney, heart, liver, pancreas, lung, brain and intestine are known to sustain damage following ischemia and reperfusion.

In ischemic preconditioning (IPC), a portion of a subject's body is subjected to brief ischemic episodes, which have been found to render tissue resistant to injuries during subsequent ischemic episodes. The phenomenon of ischemic preconditioning, first described by Murry et al., has been demonstrated in most mammalian tissues. IPC is now recognized as one of the most potent, innate, protective mechanisms against ischemia reperfusion (I-R) injury. Despite the profound protective effects demonstrable in experimental models, there are relatively few clinical reports of its effectiveness. This is, at least in part, related to the difficulty in rendering the target organ transiently ischemic prior to an intervention and the method of inducing IPC may itself induce tissue dysfunction.

Remote ischemic preconditioning (rIPC) refers to the deliberate induction of transient ischemia in a subject at a position remote from at least some of the tissue to be protected. Often, rIPC includes inducing transient ischemia at a subject's limb, to protect organs remote from the limb. Remote ischemic preconditioning (rIPC) was first described by Przyklenk et al. in 1993. They showed that transient ischemia in the circumflex coronary artery territory rendered remote myocardium resistant to injury following prolonged ischemia in the left anterior coronary artery territory. Myocardial protection has been demonstrated by a variety of remote stimuli; including renal ischemia, liver ischemia, mesenteric artery ischemia, and skeletal muscle hind limb ischemia.

Remote ischemic preconditioning has been carried out with a sphygnamometer—an instrument typically used to measure a subject's blood pressure. The cuff of the sphygnamometer is placed about the subject's arm and is inflated to a pressure great enough to occlude blood flow through the arm (i.e., pressure greater than the subject's systolic blood pressure). The cuff is maintained in the inflated state to prevent blood flow through the limb for a doctor-specified period of time, referred to herein as the ischemic duration. After the ischemic duration, pressure is released from the cuff to allow reperfusion of blood through the limb for a period of time that is referred herein as the reperfusion duration. The cuff is then re-inflated and the procedure is immediately repeated a number of times specified by a doctor.

Using a sphygnamometer or other manual type tourniquet to perform rIPC can pose some difficulties. Such approaches typically require a doctor, nurse, or other medical professional to perform the procedure. Moreover, the doctor or nurse is required to remain present during the entire remote ischemic preconditioning procedure, which may extend upwards of an hour or more. Remote ischemic preconditioning protocols may vary extensively from subject to subject or even from treatment to treatment for a given subject, which may cause confusion among those that administer the treatment.

Blood pressure measurement systems exist; however, such systems are inadequate for performing rIPC, for at least several reasons. The systems are not configured to hold pressure about a subject's limb for an extended duration and cannot cycle between ischemic and reperfusion durations as may be required when remote ischemic preconditioning is performed on subjects. As such, blood pressure measuring systems would still require the presence of a medical professional if used for rIPC to monitor or otherwise restart the blood pressure measurement process for every cycle necessary during the entire rIPC treatment.

Systems also exist for occluding blood flow through a subject's limb during surgery, so as to create a bloodless operating field. PCT publication W0 83/00995 describes one such system. The system maintains cuff pressure at a set point above systolic pressure, but lacks any controls for releasing the cuff and re-inflating the cuff in a manner sufficient for rIPC.

Other systems have been used to produce external counterpulsation blood flow in a subject. U.S. patent application 2006-0058717 describes such a system. In external counterpulsation treatment, a series of pneumatic cuffs are wrapped about a subject's limbs and are inflated and deflated in a manner that creates a pressure wave which increases bloodflow to the subject's heart. The inflation and deflation cycles are timed to the subject's heart beat, instead of longer durations typically used in rIPC. In this regard, external counterpulsation treatment systems are inadequate for performing (rIPC).

The applicants have identified that there is a need for providing a system to perform rIPC without requiring the constant presence of a medical professional.

SUMMARY

According to one aspect of the invention, a system for remote ischemic preconditioning is disclosed. The system comprises a cuff configured to contract about a limb of a subject. An actuator is connected to the cuff and, when actuated, causes the cuff to contract about the limb of the subject to reduce blood flow through the limb. A controller controls the actuator according to a treatment protocol that includes a plurality of treatment cycles. Each treatment cycle comprises cuff actuation, during which the actuator contracts the cuff about the limb of the subject to a pressure above systolic pressure to occlude blood flow through the limb and an ischemic duration, during which the actuator maintains the cuff contracted about the limb at a set point above systolic pressure to occlude blood flow through the limb. The ischemic duration lasts for at least five seconds. Each treatment cycle also comprises cuff release, during which the actuator releases the cuff to allow blood flow through the limb, and a reperfusion duration, during which the cuff is maintained about the limb in a relaxed state to allow blood flow through the limb. The reperfusion duration lasts for at least a minute or so.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF THE FIGURES

The accompanying drawings are not intended to be drawn to scale. In the drawings, each identical or nearly identical component that is illustrated in various figures is represented by a like numeral. For purposes of clarity, not every component may be labeled in every drawing.

Various embodiments of the invention will now be described, by way of example, with reference to the accompanying drawings, in which.

DETAILED DESCRIPTION

Aspects of the invention relate to a system that can provide can provide a safe and reliable method of performing remote ischemic preconditioning. The system is capable of executing a treatment protocol that has been defined by a medical professional, with minimal or no oversight by the medical professional. Embodiments of the system include features to safeguard the subject and to monitor compliance with a treatment protocol.

Figure 1:
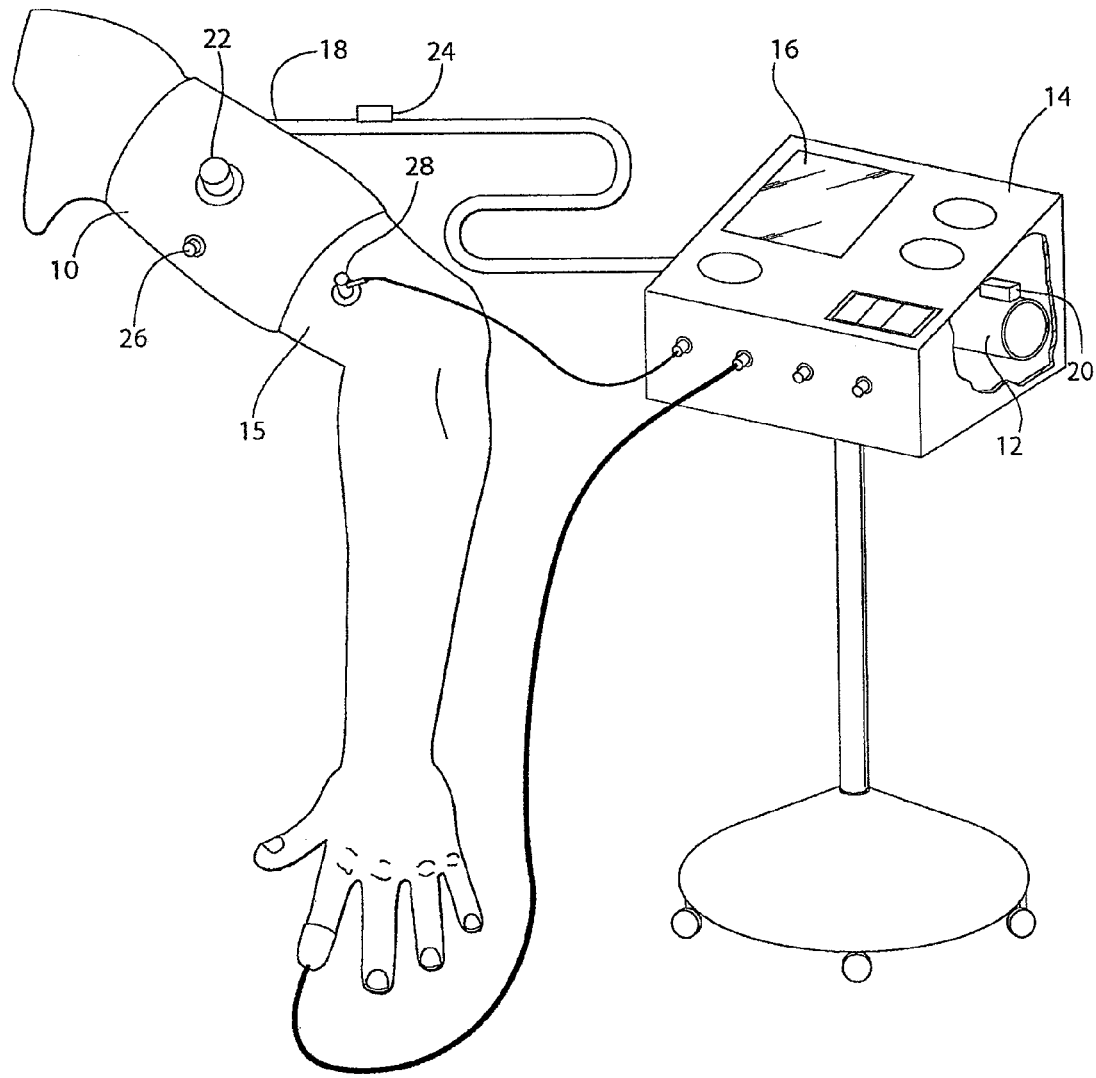
FIG. 1 is a schematic representation of one embodiment of a remote ischemic preconditioning system, including a pneumatically inflatable cuff configured to contract about the limb of a subject.

The overall system, as exemplified in FIG. 1, includes a cuff 10, an actuator 12, a controller 14 and a user interface 16. The cuff is configured to be placed about the limb 15 of a subject, such as an arm or leg of the subject. The actuator, when actuated, causes the cuff to retract about the limb to occlude bloodflow through the limb. The controller executes a treatment protocol that comprises repeating a treatment cycle one or more times. The treatment cycle itself includes: actuating the cuff to prevent bloodflow, maintaining the cuff in an actuated state for an ischemic duration, releasing the cuff, and maintaining the cuff in a relaxed state to allow reperfusion.

Figure 2:
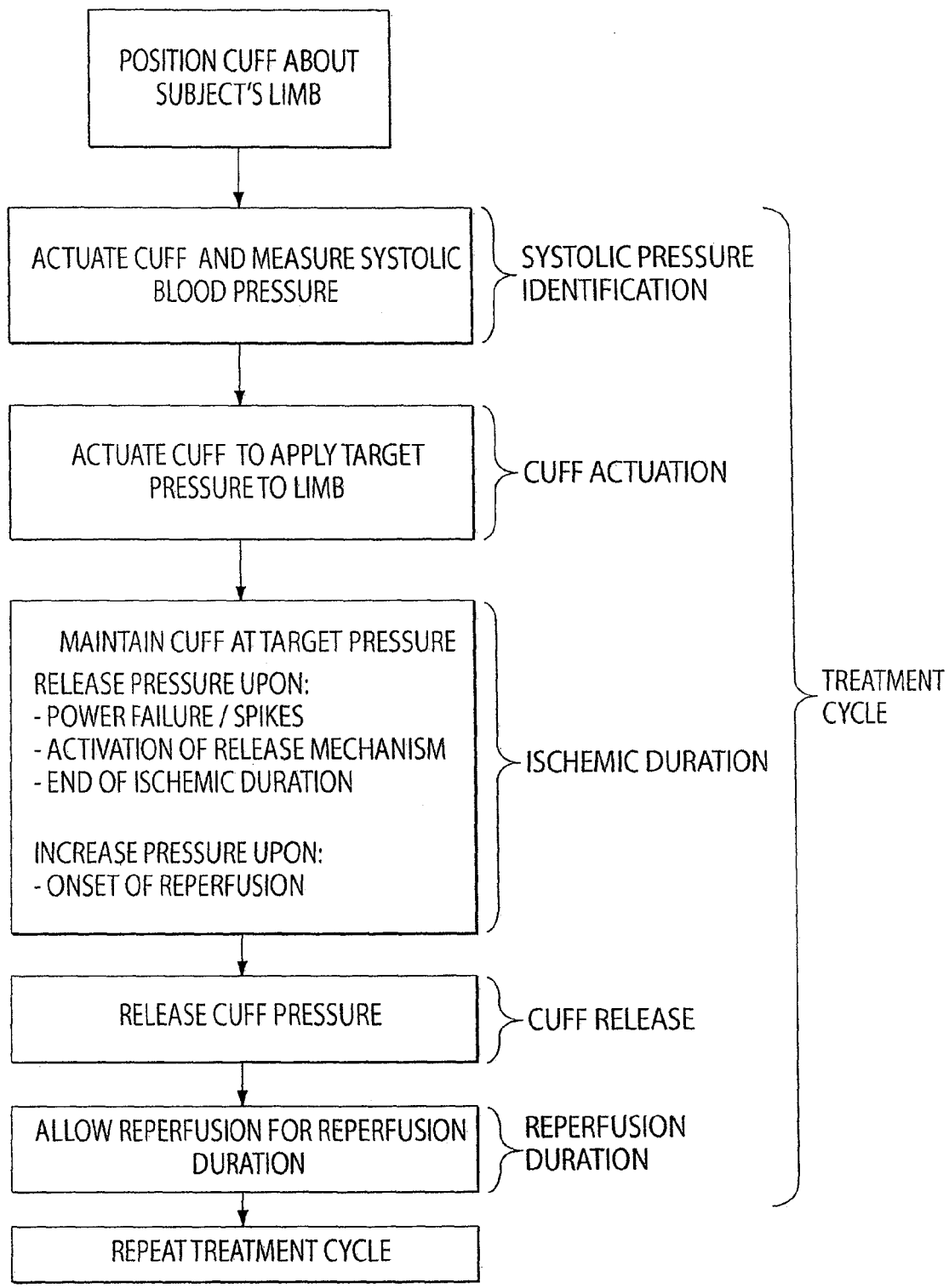
FIG. 2 is a block diagram of one embodiment of an operating scheme of the rIPC system.

FIG. 2 shows a block diagram that represents an operating scheme that may be used to perform rIPC, according to one illustrative embodiment of the invention. The scheme begins with placement of a cuff about a subject's limb. The system is then activated and the treatment protocol is initiated through the controller. In one embodiment, the system is activated by a medical professional. In another embodiment, the system may be activated by the subject himself or herself. The cuff contracts to apply an initial pressure, greater than systolic pressure, to the subject's limb. As discussed herein, the initial pressure may be a default value of the system or may be programmed into a particular treatment protocol. The cuff then deflates to identify the subject's systolic pressure by monitoring the subject for the onset of Korotkoff sounds or vibrations. Once systolic pressure has been identified, the system initiates the first treatment cycle of the treatment protocol. In some embodiments, systolic pressure may be identified as an initial portion of the treatment protocol.

The treatment cycle begins as the cuff contracts to apply a target pressure, greater than the subject's systolic pressure by an amount defined in the treatment protocol, to the subject's limb. This occludes blood flow through the subject's limb. The external pressure against the subject's limb is held for an ischemic duration defined in the treatment protocol. The system monitors the subject during the ischemic duration for pressure release criteria, which may include system power failure, system power spikes, and manual activation of quick release mechanism. The system also monitors the subject during the ischemic duration for any signs of reperfusion through the subject's limb, and accordingly, increases the external pressure applied by the cuff to prevent such reperfusion. Signs of reperfusion can include the onset of Korotkoff sounds or vibrations. After passage of the ischemic duration, the cuff releases pressure from about the subject's limb to allow reperfusion. Reperfusion is allowed for a reperfusion duration defined in the treatment cycle.

The initial treatment cycle may conclude with the passage of the reperfusion duration. At this time, a subsequent treatment cycle may begin as the cuff is actuated to contract about the subject's limb to occlude blood flow through the limb for another ischemic duration. Data collected during the prior treatment cycle may be recorded for any one or more of a variety of reasons, including but not limited to, aiding a medical professional with determining the extent of the subject's compliance with the treatment protocol, logging blood pressure data, aiding with medical research, and the like.

The cuff illustrated in FIG. 1 is configured to be positioned about the limb of a subject and to contract about the limb when actuated. In one embodiment, the sleeve is wrapped about a subject's upper arm, calf, or thigh and is fastened snuggly in place. Portions of the cuff may include hook and loop type material that can be used to fasten the sleeve in place about the subject's limb. The actuator inflates the cuff such that the limb is constricted to the point of occluding blood flow through the subject's limb.

The illustrated cuff includes an inflatable bladder (not shown) that receives a fluid, such as air, to cause the cuff expand and retract about a subject's limb. The bladder is constructed of an air impermeable material, such as flexible plastic or rubber. A connection port 18 is present at one end of the bladder to allow air to enter the bladder during inflation, or to exit the bladder during deflation. The port may include engagement features to facilitate a connection to the actuator, such as by an air hose. These features may include threads, clips, and the like. Although the illustrated embodiment includes a single bladder positioned within a cuff, it is to be appreciated that other embodiments are also possible. By way of example, according to some embodiments, the fabric sleeve may itself be air impermeable, such that no separate bladder is required. In other embodiments, multiple, separate inflatable bladders may be incorporated into a common sleeve, as aspects of the present invention are not limited in this respect.

The general size of subjects that undergo rIPC treatment may vary greatly, from sizes associated with neonatal infants to those associated with obese adults. Given this variance, it may be desirable for some embodiments of cuffs to be adjustable over a wide range to accommodate the variety of subject limb girths that may be expected. According to some embodiments, the cuff comprises an inflatable fabric sleeve having a length greater than three feet, such that a girth of up to three feet may be accommodated. Embodiments of cuffs may include a width as small as two inches, one inch, or even smaller, so as to accommodate the upper arm or leg of a much smaller subject, including a neonatal infant. It is to be appreciated, however, that other embodiments may be configured to encircle a much smaller range of limb sizes, as aspects of the present invention are not limited in this regard.

Various devices may be used as an actuator to constrict the cuff about a subject's limb, or to release the cuff. As illustrated in embodiment of FIG. 1, the actuator includes a pneumatic pump to provide pressurized air to an inflatable cuff through an air hose. The actuator also includes a release valve 20 that, when actuated, opens a passageway between the inflatable cuff and the external environment to allow pressurized air to escape from the cuff, so that the cuff loosens about the subject's limb.

The air pump can comprise any device capable of delivering compressed air. According to some embodiments, the air pump includes a piston compressor, although other types of pumps, like centrifugal pumps and scroll compressor may also be used. The pump may be configured to provide air flow at a rate of between 0.1 to 20 cubic feet per minute, with a head pressure of up to 50 psi, according to some embodiments. However, other flow rates and/or pressures are possible, as aspects of the invention are not limited in this respect.

As discussed above, the actuator may also include a release mechanism to release a cuff from about the subject's limb. In the illustrated embodiment, the release comprises a release valve 20 that is positioned within the controller housing. The release valve, as shown, may be a solenoid operated and can move rapidly between fully closed and fully open positions to rapidly release air from the cuff and, in turn, to rapidly release the cuff from a subject. According to some embodiments, the same release valve or another release valve may also be actuated to open slowly, such as to adjust the pressure of the cuff or to allow a more controlled release of pressure such as may be required when the subject's blood pressure is measured.

Embodiments of the system may include safety features to allow rapid release of the cuff from a subject's limb. Moreover, some of these embodiments may be readily activated by a subject, such as when the subject feels discomfort. In one embodiment, the safety release 22 includes a large button positioned on or near the cuff. In this regard, the safety release is within reach of the subject. In other embodiments, the safety release may comprise a separate actuator, such as one that may be held in the free hand of the subject. Activating the safety release may cause the release valve of a pneumatic cuff to open, thereby allowing rapid removal of air from the cuff.

The system may also include a continually operating, cuff release mechanism. By way of example, a slow release valve may be incorporated into a pneumatic cuff to provide for a continual, slow release of pressurized air from the cuff. The continual slow release mechanism may provide for the safe release of a subject's limb, even in the face of power failures or other events that may prevent redundant safety features from operating properly. Similar type mechanism may be incorporated into embodiments that do not utilize a pneumatically inflatable cuff, as continual slow release mechanisms are not limited to pneumatic cuffs.

Embodiments of the system include a controller that receives information from a treatment protocol and any other sensors in the system to, in turn, control the actuator to perform remote ischemic preconditioning. The controller and treatment protocol combination may be implemented in any of numerous ways. For example, in one embodiment the controller and treatment protocol combination may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the functions discussed herein. The one or more controllers can be implemented in numerous ways, such as with dedicated hardware, or with general purpose hardware (e.g., one or more processors) that is programmed using microcode or software to perform the functions recited above. The one or more controllers may be included in one or more host computers, one or more storage systems, or any other type of computer that may include one or more storage devices coupled to the one or more controllers. In one embodiment, the controller includes a communication link to communicate wirelessly, or via electrical or optical cable, to a remote location.

In this respect, it should be appreciated that one implementation of the embodiments of the present invention comprises at least one computer-readable medium (e.g., a computer memory, a floppy disk, a compact disk, a tape, etc.) encoded with a treatment protocol in the form of a computer program (i.e., a plurality of instructions), which, when executed by the controller, performs the herein-discussed functions of the embodiments of the present invention. The computer-readable medium can be transportable such that the treatment protocol stored thereon can be loaded onto any computer system resource to implement the aspects of the present invention discussed herein. In addition, it should be appreciated that the reference to a treatment protocol or controller which, when executed, performs the herein-discussed functions, is not limited to an application program running on a host computer. Rather, the term treatment protocol is used herein in a generic sense to reference any type of computer code (e.g., software or microcode) that can be employed to program a processor to implement the herein-discussed aspects of the present invention.

The system may also comprise one or more sensors 26 that receive information from the subject and/or portions of the system itself. Such sensors may receive information regarding blood flow in any portion of the subject, including the limb that is being treated. These sensors may also receive information regarding other operating parameters of the system, such as air pressure within a pneumatic cuff, direct readings of pressure applied by cuff, or tension within portions of a tension band.

Pneumatic cuffs may include a sensor to measure pressure within the cuff. Cuff pressure is often directly indicative of the pressure that exists within a blood vessel of the limb beneath the cuff. The controller of a system is often programmed to target a particular cuff pressure that is to be maintained during the ischemic duration of a treatment cycle, as is discussed herein. In embodiments that include a pneumatic cuff, the pressure sensor may be positioned anywhere within the pressurized space of the cuff, the air hose, or even within the actuator itself. Pressure sensors may also be positioned on an inner surface of the cuff to directly measure the pressure between the cuff and an outer surface of the subject's limb. In use, the cuff may be oriented such that the pressure sensor is positioned directly above the subject's artery, so as to provide a more direct measurement of pressure at a blood vessel of interest.

In one embodiment, systems may also include one or more vibration and/or ultrasonic sensors 28 to identify Korotkoff sounds. Korotkoff sounds are generally understood to be present when pressures between systolic and diastolic are externally applied to the artery of a subject. Systolic pressure is associated with a pressure value that completely occludes blood flow through a subject's blood vessels, and in this regard, may be used by the system as feedback to identify when pressure in the system is low enough to allow blood flow, or high enough to occlude blood flow.

One or more sensors may be included to confirm the cessation of blood flow or reperfusion in the limb that receives the cuff. For instance, in some embodiments, a pulse oximeter 30 may be positioned on a distal portion of the limb that receives the cuff, such as on a finger or toe of the limb. The pulse oximeter can provide information regarding blood pulsing through the subject's blood vessels and the percentage of haemoglobin that is saturated with oxygen. The pulse oximeter will detect an absence of pulses when blood flow though a limb is not occurring to confirm the occlusion of blood flow. Moreover, the pulse oximeter may also detect the percentage of haemoglobin saturated with oxygen, which will drop as blood flow through the limb ceases. It is to be appreciated that other sensors may also be used to confirm the cessation of blood flow, such as a photoplethysmographic transducer, an ultrasonic flow transducer, a temperature transducer, an infrared detector, and a near infrared transducer, as aspects of the invention are not limited in this respect.

As mentioned above, the system includes a treatment protocol that, through the controller, directs the operation of the system. Embodiments of the treatment protocol include a treatment cycle that comprises cuff actuation, an ischemic duration, cuff release, and a reperfusion duration. In many embodiments of treatment protocols, the treatment cycle may be repeated multiple times. Additionally, some embodiments of the treatment protocol include systolic pressure identification.

The cuff actuation portion of the treatment cycle comprises contracting the cuff about the limb of a subject to occlude blood flow through the limb. Contraction of the cuff is accomplished by the controller reading instructions from the treatment protocol, such as a target set point for cuff pressure, and then by the initiating the controller to bring the cuff to the target set point. Attainment of the target set point may be sensed through any of the herein described sensors and techniques.

During the ischemic phase of the treatment cycle, pressure is maintained about the subject's limb to prevent reperfusion of blood flow through the limb. The length of the ischemic phase, termed the ischemic duration, is typically defined by a doctor, or other medical professional, and is programmed into the treatment protocol. Ischemic duration may be as short as a few seconds, or as long as 20 minutes, or even longer, as aspects of the invention are not limited in this regard. In some embodiments, the ischemic duration varies from treatment cycle to treatment cycle during the same treatment protocol, although in other embodiments, the ischemic duration remains constant.

The controller acts to maintain pressure, applied by the cuff, at a set point above the subject's systolic pressure. Embodiments of the cuff may relax relative to the subject's limb over time, thereby reducing pressure and eventually allowing reperfusion. This may be caused by various factors, including relaxation of muscles in the subject's limb, stretching of the cuff about the limb, air leaks (intentional or unintentional), and the like. To this end, a sensor may provide pressure readings as feedback to the controller. The controller can measure any difference between the set point and the actual pressure reading and can provide any necessary commands to the actuator to compensate for errors.

Various approaches may be used to define an appropriate set point for the controller during the ischemic duration. According to one embodiment, the set point is manually entered into the treatment protocol by the doctor (or other medical professional). Alternately, the doctor may select a set point in terms of the subject's systolic blood pressure. In one embodiment, the set point may be selected as a fixed pressure amount over the subject's systolic blood pressure, such as 5 mm Hg, 10 mm Hg, 15 mm Hg, 20 mm Hg, 25 mm Hg, 30 mm Hg, or any other fixed amount above systolic pressure of the subject. In other embodiments, the set point may be defined as a percentage of the subject's systolic blood pressure, such as 102% of systolic, 105%, 110%, 115%, and other percentages, as aspects of the invention are not limited in this respect. The point above systolic pressure may be set by the medical professional and may be dependent upon several factors including, but not limited to the size of the subject, the size of the subject's limb, the subject's blood pressure, confirmation of blood flow cessation, and the like.

The treatment protocol, according to some embodiments, includes phases to identify the subject's systolic blood pressure. The cuff may be allowed to loosen about the subject's limb, from a point believed to be above systolic pressure, in a systematic manner while sensors are monitoring the limb for the onset of Korotkoff sounds or vibrations. Once the systolic pressure is identified, the treatment protocol may continue in the normal course.

Identification of systolic pressure may optionally occur at any time during a treatment protocol, or not at all. According to some embodiments, each treatment cycle begins with the identification of the subject's systolic blood pressure. In other embodiments, systolic pressure may be identified only once during an initial portion of the treatment protocol. In still other embodiments, systolic pressure may be identified as the cuff is released during the cuff release portion of each treatment cycle. Still, as discuss herein, systolic pressure may not be identified at all during a treatment protocol, as aspects of the invention are not limited in this regard.

The system can be configured to adjust the pressure set point during the ischemic duration. As discussed herein, the system may include sensors that detect the onset of reperfusion, such as may be indicated by the presence of Korotkoff sounds or vibrations. The presence of Korotkoff sounds during an ischemic duration can indicate that either cuff pressure has fallen below systolic or that systolic pressure has risen above the set point that was previously above systolic pressure. In such a situation, the controller may adjust the set point based on the newly identified systolic pressure and/or other information and in this regard, can identify and prevent unwanted reperfusion that might otherwise occur.

The cuff release portion of a treatment cycle occurs at the end of the ischemic duration and includes release of the cuff to a point below diastolic pressure. According to some embodiments, cuff release comprises releasing the pressure or tension of the cuff. In embodiments that utilize a pneumatic cuff, this may simply be associated with moving an air release valve to the fully open position to allow a rapid reduction in cuff pressure and a corresponding rapid relaxation of the cuff about the subject's limb. However, it is to be appreciated, that in other embodiments, that cuff relaxation may occur in a slower, more controlled manner, as aspects of the invention are not limited in this respect. Additionally, as discussed herein, the cuff release may be accompanied by monitoring for the onset of Korotkoff sounds or vibrations to identify or confirm the systolic pressure of the subject.

The reperfusion duration follows the cuff release in embodiments of the treatment cycle. Reperfusion through the limb is allowed for a period of time termed the reperfusion duration. Much like the ischemic duration, reperfusion may be allowed for varied lengths of time, as short as a five seconds, one minute or more, and as long as 20 minutes, or even longer. The reperfusion duration may remain constant from treatment cycle to treatment cycle during a common treatment protocol, or may vary between each treatment cycle, as aspects of the invention are not limited in this respect.

The treatment protocol may comprise any number of treatment cycles. As discussed herein, a common treatment cycle may simply be repeated a plurality of times, such as two, three, four, or more times, to complete a treatment protocol. Alternately, the treatment cycles of a treatment protocol may be programmed with different parameters, such as different ischemic durations, reperfusion durations, pressure set points during the ischemic duration, and the like.

In some embodiments, the system includes features to ensure subject compliance with a treatment regime. By way of example, embodiments may include a data logging feature that records the system parameters, such as cuff pressure or tension, during all phases of a treatment protocol. Date of time of operation may also be recorded. In this regard, a record may be kept of the actual use of the system so that a doctor can confirm the extent of subject compliance. Other features, such as personal information to identify the patient, may also be recorded by the system.

Embodiments of the system may incorporate various features to inform the subject or medical professional about the progress of the treatment protocol. Audible or visual indicators may accompany any of the phases of the treatment protocol. By way of example, a clock may show either the amount of time that has elapsed or that remains for a given portion of the treatment protocol or the entire protocol. Embodiments may also include other features to keep the subject and/or medical professional informed, as aspects of the invention are not limited in this regard.

According to some embodiments, the system includes features to prevent tampering or accidental reprogramming by a subject. By way of example, in some embodiments, the reprogrammable features may only be accessed after entering a code. This can prevent a subject from mistakenly reprogramming the treatment protocol or otherwise interfering with the operation of the system. It is to be appreciated that other devices may also be used to prevent accidental reprogramming, such as electronic keys, mechanical locks and the like.

The system may be configured for use is a variety of environments. By way of example, the system may be mounted on a portable stand with casters to facilitate easy movement about a healthcare facility, like a hospital. The stand may position the controller, user interface, and connections to the cuff at a convenient height for the subject and/or a doctor or nurse who may be supervising the subject. In other embodiments, the system is configured for portable use outside of a medical facility. In such embodiments, the system may be configured for ready placement into a suitcase for easy transport. Still, other embodiments may not be configured to be portable, as aspects of the invention are not limited in this respect.

Figure 3:
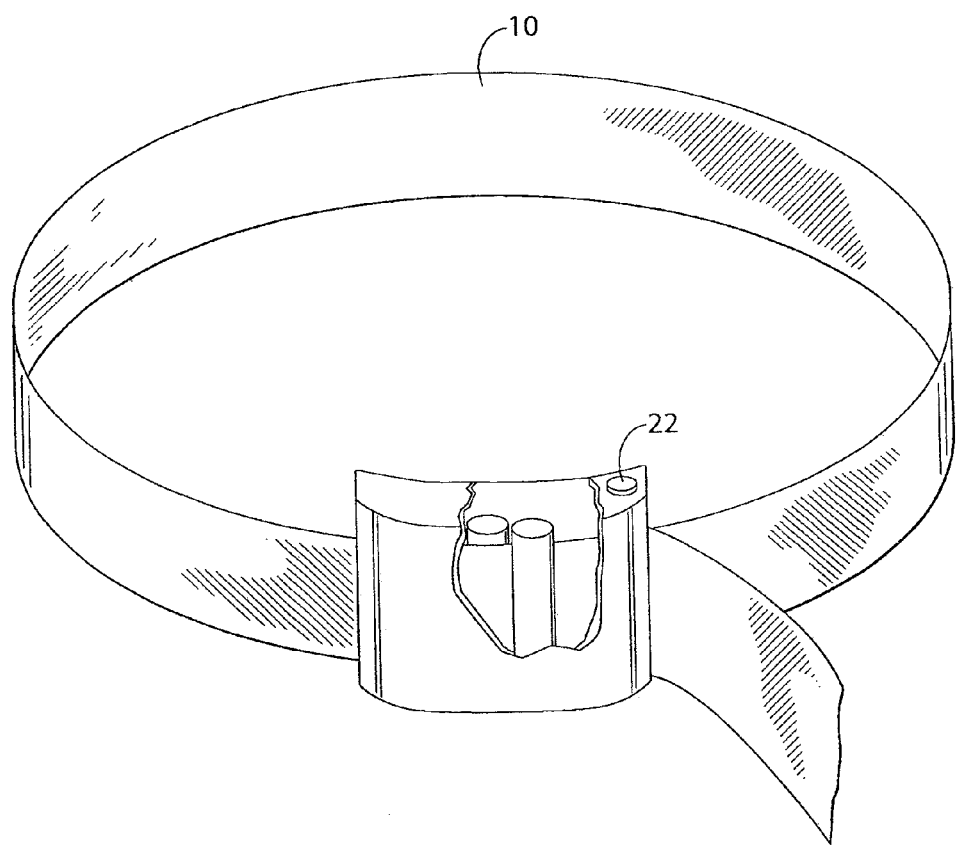
FIG. 3 shows an alternate embodiment of a cuff configured to contract about the limb of a subject.

The system is also not limited to components illustrated in the embodiment of FIG. 1. by way of example, according to other embodiments, like that illustrated in FIG. 3, cuffs may be configured to constrict a subject's limb through alternative mechanisms. In the illustrated embodiment, the cuff is configured as a band having a ratcheting mechanism positioned at one end. In use, the band is wrapped about the limb of a subject with the free end of the band passing through the ratcheting mechanism. In such an embodiment, the actuator may comprise a mechanism that pulls the free end of the band further through the ratcheting mechanism to retract the cuff about the limb, or that frees the ratcheting mechanism to release the band to, in turn, release the band from the limb.

Still other mechanisms, such as tourniquet mechanisms, are possible, as aspects of the invention are not limited in this respect.

As described above with reference to FIG. 3, some embodiments may have a cuff that comprises a band that does not inflate, but rather is tightened about a subject's limb by another mechanism. In such embodiments, the actuator may comprise a tensioning mechanism configured to move one end of the band relative to other portions of the band so as to place the band in tension. As shown, the mechanism can include opposed rollers held in close proximity to one another within a housing. The housing includes a slot for receiving a free end of the band and a fixation point for fixed attachment to the opposite end of the band. The free end of the band is passed into the slot and between the rollers. The rollers may be mechanically actuated to rotate relative to one another, such as by an electric motor, to pull the free end through the housing and thus tighten the band around a subject's limb.

The tensioning mechanism may include opposed rollers mounted on a ratcheting, free wheel mechanism. The freewheel mechanism allows the band to be pulled through the slot in one direction with minimal resistance so that the band may be pulled rapidly to a snug position about a subject's limb. The free wheel mechanism also prevents the band from moving through the slot in the loosening direction, unless the mechanism is released or the opposed rollers are actuated. It is to be appreciated that not all embodiments will include a free wheel mechanism, as aspects of the invention are not limited in this regard.

The opposed rollers rotate in either direction to tighten and loosen the band during use. When required, the rollers may rapidly rotate until the band achieves a particular tension. The rollers may further be actuated to make minor adjustments to the tension in the band during use. When the cuff is to be released from the subject's limb, a ratcheting mechanism or clutch may be released such that the opposed rollers are allowed to move freely, thus rapidly releasing tension.

Aspects of the invention are not limited to the embodiments of cuffs illustrated herein. By way of example, in some embodiments, the cuff may be positioned in direct contact with the artery of a patient, such as through intraoperative placement.

Embodiments of the present invention may be useful whenever it is desirable to prevent, inhibit altogether, or reduce the possibility or severity of ischemic injury. Embodiments of the invention contemplate both therapeutic and prophylactic treatment of subjects. The methods of treatment disclosed herein can be used to reduce ischemic injury in organs including but not limited to the heart, brain, kidney, pancreas, lung, intestine and the like. Further details regarding the physiological mechanisms of remote ischemic preconditioning may be found in the co-owned U.S. patent application 60/857,918 entitled Anti-Ischaemic Agent filed on Nov. 10, 2006 under express mail label number EV492322827US, which is hereby incorporated by reference in its entirety.

The foregoing written specification is considered to be sufficient to enable one ordinarily skilled in the art to practice the invention. The present invention is not to be limited in scope by examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

What is claimed is:

1. A system for remote ischemic preconditioning, the system comprising:
    a cuff configured to retract about a limb of a subject;
    an actuator connected to the cuff and that, when actuated, causes the cuff to contract about the limb of the subject to reduce blood flow there through; and
    a controller that controls the actuator to operate according to a treatment protocol that includes a plurality of sequentially actuated treatment cycles, each treatment cycle comprising:
        cuff actuation, during which the actuator contracts the cuff about the limb of the subject to a pressure above systolic pressure to occlude blood flow through the limb;
        an ischemic duration, during which the actuator maintains the cuff contracted about the limb at a set point above systolic pressure to occlude blood flow through the limb, the ischemic duration lasting for at least about a minute;
        cuff release, during which the actuator releases the cuff to allow blood flow through the limb; and
        a reperfusion duration, during which the cuff is maintained in an at least partially relaxed state to allow blood flow through the limb, the reperfusion duration lasting for at least one minute.

2. The system according to claim 1, wherein the treatment protocol further comprises:
    systolic pressure identification.

3. The system according to 2, wherein systolic pressure identification is performed prior to an initial treatment cycle.

4. The system according to claim 2, wherein systolic pressure identification occurs during each of the plurality of treatment cycles.

5. The system according to claim 1, wherein the ischemic duration comprises further actuation by the actuator to maintain pressure applied by the cuff at the set point.

6. The system according to claim 5, wherein the set point is approximately 10 mm Hg above systolic pressure of the subject.

7. The system according to claim 5, wherein the set point of the ischemic phase is approximately 20 mm Hg above systolic pressure of the subject.

8. The system according to claim 5, wherein the set point is approximately 30 mm Hg above systolic pressure of the subject.

9. The system according to claim 1, further comprising:
    a transducer that identifies reperfusion through the limb, wherein the controller receives a signal from the transducer during the ischemic phase to confirm a lack of reperfusion.

10. The system according to claim 9, wherein the controller receives a signal from the transducer during the reperfusion phase to confirm reperfusion through the limb.

11. The system according to claim 9, wherein the transducer is selected from a group consisting of: a photoplethysmographic transducer, an ultrasonic flow transducer, a temperature transducer, an infrared detector, and a near infrared transducer.

12. The system according to claim 1, further comprising:
    a safety release configured to allow blood flow through the limb when a safety criteria is met.

13. The system according to claim 12, wherein the safety criteria includes one or more criteria selected from the group consisting of: a power outage of the system, a power spike in the system, activation of a manual release switch.

14. The system according to claim 1, wherein the treatment protocol is configured to be reprogrammable.

15. The system according to claim 1, further comprising:
    an interface to be accessed by the subject, the user interface providing controls that allow the subject to initiate the treatment protocol and to terminate the treatment protocol.

16. The system according to claim 14, wherein the controller includes safeguards to prevent the subject from altering the treatment protocol.

17. The system according to claim 1, further comprising:
    a data logger to record use of the system by the subject.

18. The system according to claim 1, wherein the treatment cycle is repeated five times during the treatment protocol.

19. The system according to claim 1, wherein the ischemic duration is less than 1 minute during an initial treatment cycle of the treatment protocol, and wherein the ischemic duration is greater than 1 minute in a treatment cycle that occurs subsequently during the treatment protocol.

20. The system according to claim 1, wherein the cuff is a pneumatically inflatable cuff and wherein the actuator is an air pump.

21. The system according to claim 1, further comprising:
    a bleed valve that continuously releases pressure from the cuff.

22. The system according to claim 1, configured to be portable.

23. The system according to claim 1, further comprising:
    a computer readable medium that includes the treatment protocol, and that when executed by the controller, executes the treatment protocol.

24. The system according to claim 1, wherein the treatment protocol includes three or more treatment cycles.

25. A method of performing remote ischemic preconditioning comprising:
    providing a device that includes:
        a cuff configured to retract about a limb of a subject;
        an actuator connected to the cuff and that, when actuated, causes the cuff to contract about the limb of the subject to reduce blood flow there through; and
        a controller that controls the actuator according to a treatment protocol that includes a plurality of sequentially actuated treatment cycles;
    initiating operation of the device to effect remote ischemic preconditioning of the subject by actuating the actuator according to the treatment protocol, wherein the treatment protocol comprises:
        contracting the cuff about the limb of the subject to a pressure above systolic pressure to occlude all blood flow through the limb;
        maintaining the cuff in a contracted state about the limb at a set point above systolic pressure to occlude all blood flow through the limb for at least about a minute;
        releasing the cuff to allow blood flow through the limb;

maintaining the cuff in at least a partially relaxed state to allow blood flow through the limb for at lest one minute; and repeating the treatment protocol.

26. The method according to claim 25, further comprising: identifying a systolic pressure level of the subject prior to initiating operation of the device.

27. The method according to claim 25, further comprising: monitoring for safety criteria; and allowing reperfusion through the limb of the subject when the safety criteria is met.

28. The method according to claim 27, wherein monitoring for safety criteria includes monitoring for a power outage to the device, a power spike to the device, and/or activation of a manual release switch.

29. The method according to claim 25, wherein initiating operation of the device includes initiation of the device by the subject.

30. The method according to claim 25, wherein initiating operation of the device to effect remote ischemic preconditioning includes initiating operation of the device according to a treatment protocol that includes five or more treatment cycles.

31. The method according to claim 25, wherein initiating operation of the device to effect remote ischemic preconditioning includes initiating operation of the device according to a treatment protocol that includes treatment cycles that each have different ischemic durations.

32. The method according to claim 31, wherein initiating operation of the device to effect remote ischemic preconditioning includes initiating operation of the device according to a treatment protocol that includes treatment cycles that each have ischemic durations greater than 30 seconds.

33. A method of performing remote ischemic preconditioning, the method comprising:

providing a system that includes:
- a cuff configured to retract about a limb of a subject;
- an actuator connected to the cuff and that, when actuated, causes the cuff to contract about the limb of the subject to reduce blood flow there through; and
- a controller that controls the actuator to operate according to a treatment protocol that includes a plurality of sequentially actuated treatment cycles, each treatment cycle comprising:
    - cuff actuation, during which the actuator contracts the cuff about the limb of the subject to a pressure above systolic pressure to occlude all blood flow through the limb;
    - an ischemic duration, during which the actuator maintains the cuff contracted about the limb at a set point above systolic pressure to occlude all blood flow through the limb, the ischemic duration lasting for at least about a minute;
    - cuff release, during which the actuator releases the cuff to allow blood flow through the limb; and
    - a reperfusion duration, during which the cuff is maintained in an at least partially relaxed state to allow blood flow through the limb, the reperfusion duration lasting for at least one minute;

positioning the cuff about the limb of the subject; and initiating operation of the device to effect remote ischemic preconditioning of the subject by actuating the actuator according to the treatment protocol.

* * * * *